(12) United States Patent
Arvai et al.

(10) Patent No.: US 6,320,085 B1
(45) Date of Patent: Nov. 20, 2001

(54) PROCESS FOR THE PREPARATION OF BENZYL-ETHERS

(75) Inventors: Geza Arvai; Bela Bertok, both of Budapest; Zsuzsanna Kuruczne Ribai; Laszlo Pap, both of Erd; Istvan Szekely, Dunakeszi, all of (HU)

(73) Assignee: Agro-Chemie Novenyvedoszer Gyarto Ertekesito est Forgalmazo Kft., Budafest (HU)

( * ) Notice: Subject to any disclaimer, the term of this patent is extended or adjusted under 35 U.S.C. 154(b) by 0 days.

(21) Appl. No.: 09/297,824

(22) PCT Filed: Nov. 12, 1997

(86) PCT No.: PCT/HU97/00073

§ 371 Date: Jul. 13, 1999

§ 102(e) Date: Jul. 13, 1999

(87) PCT Pub. No.: WO98/22416

PCT Pub. Date: May 28, 1998

(30) Foreign Application Priority Data

Nov. 18, 1996 (HU) ................................................. 9603179

(51) Int. Cl.$^7$ ............................ C07C 43/11; C07C 41/08
(52) U.S. Cl. .................. 568/607; 568/626; 568/659; 568/660; 568/661; 568/662; 568/663
(58) Field of Search .................. 568/626, 659, 568/660, 661, 662, 663, 665, 669, 607

(56) References Cited

FOREIGN PATENT DOCUMENTS

| | | |
|---|---|---|
| 1007421 | 6/1995 | (BE) . |
| 833190C | 3/1952 | (DE) . |
| 4434823 | 4/1996 | (DE) . |
| 2029290 | 10/1970 | (FR) . |

OTHER PUBLICATIONS

S. Kim et al., Journal of Organic Chemistry, vol. 52, No. 17, 1987 pp. 3917–3919.
S. Anandarman, Chemical Abstracts, vol. 109, No. 15, 1988, Abstract No. 129377b, p. 728, column 2.
J. M. Saa et al., Journal of Organic Chemistry vol. 53, No. 18, 1988, pp. 4263–4273.

*Primary Examiner*—Rosalynd Keys
(74) *Attorney, Agent, or Firm*—Birch, Stewart, Kolasch & Birch, LLP

(57) ABSTRACT

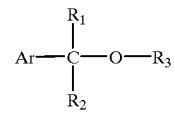

I

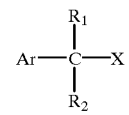

II

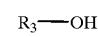

III

The subject matter of the invention is the process for the preparation of mixed ethers of formula I, wherein Ar represents an aromatic or one or more heteroatom-containing moiety, optionally substituted by one or more $C_{1-4}$ alkoxy, methylenedioxy, $C_{1-4}$ alkyl, halogen, $C_{1-4}$ haloalkyl or nitrogroup, and/or condensed with a benzene ring; $R_1$ and $R_2$ independently mean hydrogen, $C_{1-4}$ alkyl, $C_{1-4}$ haloalkyl, $C_{2-4}$ alkenyl, phenyl, substituted phenyl, $C_{3-6}$ cycloalkyl group, $R_3$ means $C_{3-6}$ alkynyl, optionally substituted by one or more $C_{1-6}$ alkyl, $C_{3-6}$ alkenyl, $C_{3-6}$ alkynyl, $C_{1-6}$ haloalkyl group, or halogen atom, $R^3$ also means a $C_{1-4}$ alkyloxy-$C_{1-4}$ alkyloxy-$C_{1-4}$ alkyl group. The process comprises the step of reacting the compounds of general formula II with 1 to 3 molar equivalent of the alcohol of general formula III in the presence of acid, a Lewis acid, a metal oxide or a metal carbonate, X means hydroxy, halogen or sulphonester leaving group, the resulting ether of general formula I is isolated, if desired, stabilized by the addition of a base and/or an antioxidant; and if desired the excess of the alcohol is recovered.

17 Claims, 1 Drawing Sheet

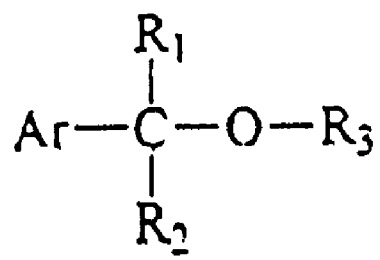
I.
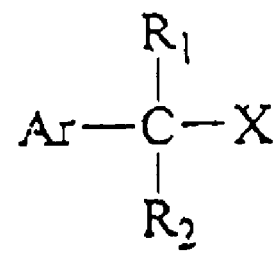
II.
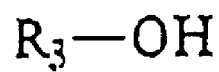
III.

PROCESS FOR THE PREPARATION OF BENZYL-ETHERS

This application is the national phase under 35 U.S.C. §371 of PCT International Application No. PCT/HU97/00073 which has an International filing date of Nov. 12, 1997 which designated the United States of America.

SUMMARY OF THE INVENTION

This invention relates to the process of preparation of mixed ethers of general formula I, wherein Ar represents an alicyclic, aromatic or one or more heteroatom-containing heterocyclic moiety, optionally substituted by one or more $C_{1-4}$ alkoxy, methylenedioxy, $C_{1-4}$ alkyl halogen, $C_{1-4}$ haloalkyl or nitro-group, and/or condensed with a benzene ring, $R^1$ and $R^2$ independently mean hydrogen, $C_{1-4}$ alkyl, $C_{1-4}$ haloalkyl, $C_{2-4}$ alkenyl, phenyl, substituted phenyl, $C_{3-6}$ cycloalkyl group, $R^3$ means $C_{3-6}$ alkynyl group, optionally substituted by one or more $C_{1-6}$ alkyl, $C_{3-6}$ alkenyl, $C_{3-6}$ alkynyl, $C_{1-6}$ haloalkyl group, or halogen atom; or a $C_{1-4}$ alkyloxy-$C_{1-4}$alkyl-oxy-$C_{1-4}$alkyl group, under acidic conditions, by the reaction of compounds of general formula II, wherein X means hydroxy, halogen or sulfonester leaving group, with compounds of general formula III, wherein $R^3$ has the same meaning as above.

In the term Ar the aromatic group is favourably phenyl or naphthyl group, Ar as a heterocyclic moiety may contain one or more O, S, N heteroatoms, it may favourably represent benzodioxole-, benzodioxane-, 2-benzofuran-, 7-benzofuran-moieties.

The alicyclic group may favourably be condensed with a benzene ring, thus for instance may represent indane group, or 1,2,3,4-tetrahydronaphthyl group. The carboximide group may favourably represent phthalimide moiety. The aromatic, heterocyclic and alicyclic Ar groups are optionally substituted by $C_{1-4}$ alkoxy-, methylenedioxy-, $C_{1-4}$ alkyl-, halogen-, $C_{1-4}$ haloalkyl- or nitro group.

FIELD OF THE INVENTION

The ethers of general formula I are potential starting materials or active ingredients of a number of chemical products. Several representatives of them are arthropodicide synergists of outstanding activity (Hungarian patent application No 3318/95). With the exception of the methylenedioxy (MDP) synergists having saturated side-chain (such as PBO, i.e. 5-[2-(2-butoxyethoxy)ethoxymethyl]-6-propyl-1,3-benzodioxol), which have been known, the compounds are new, irrespective of their simple structures. Owing to their outstanding significance, their preparation and economical synthesis is of great importance.

BACKGROUND OF THE INVENTION

The above ethers can be prepared by the general methods known for the synthesis of ethers (Gy. Matolesy, M. N ádasdy, V. Andriska; *Pesticide Chemistry*, Akadémia (1988); Hungarian patent specifications No 3318/95). The essence of these methods is to react the alkali salt of the alcohol component with the partner, according to the rules of the nucleophilic substitution. The partner contains a leaving group, which is usually a halogen, preferably bromo atom. The reaction may be accomplished in two ways, depending on which part of the molecule is the nucleophilic partner.

Due to the greater reactivity of benzyl halogenides, in the practice usually the alcoholate of the side-chain is reacted with benzyl bromide. This method is, however, limited when the alcoholate is for some reason hard to prepare. In these cases the inverse method may bring solution, but usually poorer reactions can be expected. This sort of ether preparation is known in the organic chemistry as the classical Williamson synthesis (B. P Mundy, M. G. Ellerd, *Name Reactions and Reagents in Organic Synthesis*, Wiley (1988)).

The reaction has, however, several drawbacks. The formation of the alcoholate is costly for the industry, it requires expensive reagents and refined technology with guaranteed water-free conditions or with a drying step (Hungarian patent applications No. 180500, 190842).

The preparation of the halogenide or of the partner containing the leaving group requires a separate step and the use of further costly reagents. In case the alpha carbon atom contains additional substituents ($R^1$ and/or $R^2$ is different from hydrogen) the preparation of the activated, for example halogen derivative involves difficulties as the product is susceptible to elimination reaction or side reactions, for instance aromatic electrophilic substitution. The yield of the coupling strongly depends on the reactivity of the partner and the resulting product needs further purification.

For the preparation of ethers in general, further methods are also known. The oldest and most well-known among them is the acid catalyzed dimerisation of alcohols (Houben Weyl 6/3 11–19). According to the literature the reaction usually requires high temperature and to avoid decomposition the product has to be continuously removed from the reaction mixture. The oxonium cation formed on the action of the acid may easily take part in rearrangement reactions or it may be stabilized by the so called β-elimination of the hydrogen atom from the neighbouring carbon atom, giving rise to the appropriate olefine. This causes the formation of considerable amount of decomposition products, complicated by the fact that the water which is formed in the reaction slows down the process. As a consequence, the performance of the reaction (yield, purity) is low. It is understandable therefore, that this method is not counted for when a synthesis is planned. It is rather taken into consideration as a side-reaction of acid-catalyzed processes (*Chem. Pharm. Bull.* 31, 3024, (1983)).

In the case of the dibenzyl ethers, to eliminate the draw-backs, the methyl sulfoxide-induced dimerization method has been worked out (*J. Org. Chem.* 42, 2012, (1977)). Owing to the applied reagent and high temperature (175° C.), however, the method can not be utilized in industrial scale.

It was a major break-through when it was revealed that, in addition to the fact that the ether formation can be catalyzed by Lewis acids, the reaction with zinc(II) chloride in dichloroethane can be performed under relatively mild conditions (*J. Org. Chem.* 52, 3917, (1987)). The method, however, has been worked out practically only for dimerization and intramolecular cyclization reactions. For mixed ethers the reproducibility of the reaction, as well as the quality and yield of the product are poor. With benzyl(p-methoxybenzyl)alcohol, containing an aromatic substituent, the reaction proceeds in low yield due to polymerization; the mixed ether with unsaturated chain (α-methylbenzyl allyl ether)—unlike its saturated analogue—can be obtained again, only in poor yield, because of dimerization. In a published version of the reaction the benzyl halogenide was reacted with the nucleophilic reagent in the presence of zinc oxide (*Tetrahedron*, 38, 1843, (1982)), but applicability of this reaction for the compounds of general formula I is not known.

The acid-catalyzed ether formation takes place through the appropriate cationic intermediate. Stability of ring-substituted 1-phenylethyl carbocations and their reaction with nucleophilic reagents in trifluoroethanol/water=1./I model system has been studied (*J. Am. Chem. Soc.*, 106, 1361, ((1984); 106, 1373, (1984). The two references, however do not give examples on the preparation of compounds of general formula I., and do not give a hint concerning their synthesis respect to the reaction media (polarity, solvation), which—as shown by the two references—play major role in the reaction and even small modifications may disturb the sensible equilibria. Authors of the above two references in their later theoretical work have published that ethers, similar type to general formula I., are surprisingly sensible to acids, differing from other ethers. Ether formation proceeds in a reversible reaction, which increases the possibility of by-product formation, deteriorating purity and yield of the product. As shown by the data published, alkoxyalcohols, such as ethylene glycol monomethyl ether, have poor reactivity, unsaturated alcohols e,g. propargyl alcohol have medium reactivity, falling well behind the reactivity of simple saturated alcohol like methanol, ethanol and butanol, which react readily. Electron-withdrawing substituents of the aromatic ring enhance, electron-donating substituent decrease the equilibrium constant of the ether formation. Increasing the water/trifluoroethanol ratio causes unfavourable effect on the direct ether formation.

The production of the ethers is an extremely difficult task for the industry. Not only because of expensive reagents and possible side reactions, but also because both the starting alcohols and the resulting ethers easily form peroxides and are potential explosives. In addition, the alkenyl compounds, due to the triple bond, are sensible to heat. At a large scale (1000 t/year) safe production is only conceivable if the reaction can be carried out under mild conditions and the end-product, which is in most cases a liquid, does not have to be further purified, distilled.

BRIEF DESCRIPTION OF THE DRAWING

The drawing shows general formulae I, II, and III that represent aspects of the present invention.

DETAILED DESCRIPTION OF THE INVENTION

In the light of the above we investigated in details the possibilities of the preparation of asymmetric ethers of general formula I. The essence of our method which we worked out on the basis of our experimental results, is that the mixed ethers of general formula I., wherein the meaning of the substituents is the same as described above, can very favourably prepared by reacting the compounds of general formula II., wherein X means hydroxy, halogen or sulfonester leaving group, with 1–3 molar equivalent of the alcohol of general formula III., wherein the meaning of the substituents is the same as above, in the presence of an acid, Lewis acid, metal oxide or metal carbonate. The resulting ether of general formula I. is isolated, the excess of the alcohol is recovered, if desired, the product is stabilized by the addition of a base and/or an anti-oxidant. In general formulae I., II. and III. the meanings of Ar, $R^1$, $R^2$ and $R^3$ are the same as given above.

As for acids favourably 0.01–3 molar equivalent of a strong mineral or organic acid, preferably hydrochloric acid, sulfuric acid, perchloric acid or aromatic sulfonic acid is applied. The reaction is carried out in the solution of salts, preferably in the solution of sodium chloride, calcium chloride, magnesium chloride, zinc chloride, preferably in, a 10 w/w % aqueous solution of the acid, preferably saturated with the inorganic salt, and at a temperature of (−20)–(+30)° C.

As for Lewis acid preferably 0.01–3 molar equivalent of zinc(II) chloride or an aromatic sulfonic acid, preferable benzenesulfonic acid or para-toluenesulfonic acid is applied and the reaction is carried out in an apolar aprotic solvent, at a temperature of (−30)–(+40)° C.

As for metal oxide preferably 0.01–3 molar equivalent of zinc oxide, as for metal carbonate zinc carbonate is applied and the reaction is carried out without solvent or in the presence of an apolar aprotic solvent.

As for organic solvents, halogenated solvents proved to be good, among them dichloroethane was the best. In that case Lewis acid can also be used. Zinc(II) chloride, as reported in the literature, did not prove well for the preparation of structures very similar to compounds of general formula I., it resulted low yields and contaminated products (J. Org. Chem. 52, 3917, (1987)), nevertheless, in the optimized system of our invention the reaction proceeded in good yield and resulted the product with appropriate purity. Similarly, the reaction also proceeded well when using zinc oxide. The zinc halogenide by-product did not cause polimerization in that case, either. The reaction doesn't require anhydrous solvents and conditions. The water, which forms during the reaction, does not hinder the full accomplishment of the reaction, it bounds the catalyst. The resulting emulsion or suspension can be separated by simple precipitation or filtration, and following a work-up procedure it can be re-utilized.

In the industrial application the use of water as solvent is especially convenient. This version is unique not only because it has not been used earlier, but also because it is surprising, since the formation of ethers—an equilibrium reaction—was expected to be suppressed in aqueous medium. (*J. Am. Chem. Soc.*, 107, 1340 (1985)). The method, in contrast to literature data, was very good applicable even for preparation of benzyl alkynyl ethers with electron-donating (hydroxy, methoxy, ethoxy, methylenedioxy group) substituents. Benzyl ethers containing phenolic hydroxy group can also be directly, selectively synthesized, despite of the fact that they contain more than one nucleophilic centre. Enhancing the polarity of the medium is favourable. Consequently, the use of auxiliary materials, preferably the use of various salts is favourable. Selecting the right parameters the reaction can be shifted towards the formation of the product. Of the acid catalytic amount, 1–2 mol % is sufficient. The reaction is fast even at low temperature, undesired side reactions can thus be avoided. The alcohol is preferably applied in excess amount, by this way reaction time may significantly be shortened. The product may be isolated from the reaction mixture by simple sedimentation and the electrolyte may be re-used. The starting alcohol recovered from the process may be re-used. The process is thus practically quantitative for both components. The raw product obtained in the reaction is of very good quality. Its purity achieves 93–95%. It may of course be further purified by distillation, or if possible, by crystallisation but it may be used straightaway. To enhance its stability and hinder its acidic hydrolysis it is suitable to wash the product to neutral and buffer it in the basic pH region. For the sake of safer handling the addition of anti-oxidants of various type is recommended.

As for anti-oxidants e.g. TMQ; BHT; hydroquinone; hydroquinone monomethyl ether; 2,2,6,6-tetramethyl-4-piperidinol-N-oxide may preferably be used.

To demonstrate our process we give the following non limiting examples without the intention of being complete.

EXAMPLES

1.) 1-[1-(But-2-ynyloxy)ethyl]-3-hydroxy-4-methoxybenzene

A.)

1.7 g (10.7 mmol) of 1-(3-hydroxy-4-methoxyphenyl) ethanol is dissolved in 1.4 g of 2-butynol, and to that solution 1.5 ml of 1% HCl-50% $CaCl_2$ solution was added under stirring at room temperature. The mixture was stirred at that temperature overnight. The reaction was followed by TLC. (eluent: n-hexane-ethyl acetate 7:3; $R_f$=0.19). to the reaction mixture diethyl ether was added, until the oily organic phase dissolved. The mixture was then neutralized with 1M NaOH solution, the two phases were separated, the aqueous layer as twice extracted with ether, the combined or layers were washed subsequently with water and saturated sodium chloride solution, dried over $MgSO_4$, filtered and evaporated.

Yield: 2.08 g (94%) colourless, thick oil. GC (CP 9000, CP-SIL-5CB 60 m×0.53 mm, 5 ml/min $N_2$ FID, 250° C.): $t_R$=4.44 min, >93%. IR ($CHCl_3$, cm$^{-1}$) υ: 3601, 3541, 2972, 2924, 2857, 1728, 1615, 1596, 1507, 1457, 1443, 1372, 1308, 1288, 1271, 1235, 1164, 1132, 1110, 1084, 1043, 1030, 1004, 934, 877, 841, 808, 644, 611. $^1$H-NMR (200 MHz, $CDCl_3$) δ: 1.44 (3H, d, J=6.4 Hz, CH—$CH_3$), 1.84 (3H, t, J=2.2 Hz≡C—$CH_3$), 3.81 and 4.01 (2H, $ABX_3$, $J_{AB}$=15.0 Hz, $J_{AX}$=$J_{BX}$=2.34 Hz, ≡C—$CH_2$O), 3.87 (3H, s, $OCH_3$), 4.52 (2H, q, J=6.4 Hz, Ar—CHO), 5.80 (1H, OH), 6.82 (2H, d, J=1.12 Hz aromatic 5,6-CH) 6.91 (1H, t, aromatic-CH). $^{13}$C-NMR (50 MHz, $CDCl_3$) δ: 3.56 (≡C—$CH_3$), 23.65 (CH—$CH_3$), 55.84 ($OCH_3$), 55.89 (≡C—$CH_2$O), 75.35 (≡C—$CH_2$), 76.06 (Ar—CH—$CH_3$), 81.89 (≡C—$CH_3$), 110.47 (C-2), 112.66 (C-5), 118.08 (C-6), 135.93 (C-1), 145.65 (C-4), 146.08 (C-3).

B.)

The procedure is described in the previous example is followed, with the difference that instead of calcium chloride solution zinc(II) chloride solution is applied. The resulting product is identical with the product obtained in the previous process.

2.) 1-[1-(But-2-ynyloxy)ethel]-3,4-dimethoxybenzene/1-(3',4'-dimethoxypheneyl) ethylbut-2-ynyl ether/

A.)

Preparations to the Process:

In 250 ml of water 125 g of calcium chloride dihydrate is dissolved under stirring. On the basis of its density (d=1.33 g/ml) this solution equals with an approx. 35 w/w % calcium chloride solution. If necessary, the solution is filtered. In a volumetric flask 7.6 ml (9.0 g) of conc. hydrochloric acid is diluted with the previous solution to 250 ml.

Procedure:

To the vigorously stirred mixture of 500.0 g α-methylveratryl alcohol and 192.3 g 2-butyn-1-ol are added a mixture consisting of 250 ml of the calcium chloride-hydrochloric acid solution and 192.3 g of 2-butyn-1-ol is added in a fast rate. The reaction is followed by GC and TLC analysis. After 6 hours the relative amount of the of the product is 92–93%, as shown by GC analysis whereas the amount of the starting material decreases to less than 2%. Following this the reaction mixture is diluted understirring with 500 ml of ether and it is neutralized under stirring with 1M sodium hydroxide solution. After separation the aqueous layer is extracted with 2×100 ml of ether. The combined organic phase is washed with saturated sodium chloride solution (the pH of the aqueous layer is checked for neutrality), and it is dried. The solution is evaporated under atmospheric pressure. The excess of the butynol is distilled off in water jet vacuo. The recovered 182 g of butynol may be used again following investigation of purity (GC, refractive index). Product: 650 g of colourless oil.

Purity: by direct integration 93%, with octacosane internal standard 95%, yield: 94%, $n_D^{20}$ 1720 1.5280. IR ($CHCl_3$ cm$^{-1}$) υ: 2976, 2855, 2837, 1605, 1595, 1514, 1465, 1419, 1371, 1353, 1311, 1260, 1164, 1141, 1086, 1027, 864. $^1$H-NMR (200 MHz, $CDCl_3$) δ: 1.46 (3H, d, J=6.5 Hz, CH—$CH_3$), 1.85 (3 h, t, J=2.3 Hz, ≡C—$CH_3$), 3.83 and 4.01 (2H, $ABX_3$, $J_{AB}$=15.0 Hz, $J_{AX}$=$J_{BX}$=2.3 Hz, ≡C—$CH_2$—O), 3.87 and 3.89 (altogether 6H, each s, O—$CH_3$), 4.55 (2H, q, J=6.5 Hz, Ar—CH—O), 6.80–6.89 (3H, m, aromatics). $^{13}$C-NMR (50 MHz, $CDCl_3$) δ: 3.61, (≡C—$CH_3$), 23.76 (CH—$CH_3$), 55.87 (O—$CH_3$), 55.96 (≡C—$CH_2$—O), 75.36 (≡C—$CH_2$), 76.40 (Ar—CH—O), 81.91 (≡C—$CH_3$), 109.06 (C-2), 110.86 (C-5), 118.94 (C-6), 135.30 (C-1), 148.52 (C-3), 149.19 (C-4).

B.)

To a flask equipped with magnetic stirrer, condenser, and drying tube filled with calcium chloride, α-methylveratryl alcohol (8.72 g, 0.0478 mol) and 2-butyn-1-ol (4.36 g, 0.0623 mol) are added, and then dissolved in 100 ml of dichloroethane. Under stirring at room temperature zinc(II) chloride (1.97 g, 0.0145 mol) is added to the mixture. The reaction is accompanied by a characteristic change of colour. After 2 hours of reaction the aqueous part formed in the reaction is separated, the organic phase is washed with 3×30 ml of saturated sodium chloride solution, dried and evaporated. The raw product (12.1 g) is distilled in vacuo with the help of a vacuum pump. Yield: 9.2 g (0.0393 mol, 82.2%). GC (with internal standard) 98.2%. The material is identical with the compound obtained by the previous method.

3.) 1-[1-(But-3-ynyloxy)ethyl]-3,4-dimethoxybenzene

Into a flask equipped with stirrer 3.0 g of (0.0164 mol) α-methylveratryl alcohol and 2.3 g (0.0329 mol) of 3-butyn-1-ol are added, and to the mixture 1.5 ml of the solution consisting of 50 w/v % of calcium chloride-1 w/w % hydrochloric acid is added at a fast rate. The mixture is stirred overnight at room temperature. It is then diluted with ether, and the mixture is neutralized with a few drops of 1 M sodium hydroxide solution. The two phases are separated, the aqueous phase is thoroughly extracted with ether. The combined organic layers are washed with saturated sodium chloride, dried and evaporated.

Yield: 3.5 ((93%) Purity 92%. IR ($CHCl_3$, cm$^{-1}$) υ: 3307, 3027, 2958, 2933, 2869, 2838, 2120, 1607, 1595, 1509, 1465, 1443, 1259, 1163, 1142, 1098, 1027, 861. $^1$H-NMR (200 MHz. $CDCl_3$) δ: 1.45 (3H, d, J=6.5 Hz, CH—$CH_3$), 1.96 (1H, t, J=2.7 Hz, ≡CH), 2.44 (2H, td, J=7, 2.7 Hz, $CH_2$—C≡), 3.43 (2H, t, J=7 Hz), 3.87 and 3.89 (altogether 6H, each s, $OCH_3$), 4.38 (2H, q, J=6.5 Hz, Ar—CHO), 6.83 (2H, d, aromatic), 6.90 (1H, s, aromatic). $^{13}$C-NMR (50 MHz, $CDCl_3$) δ: 19.95 ($OCH_2$—$CH_2$), 24.0 (CH—$CH_3$), 55.77 and 55.82 ($OCH_3$), 66.33 ($OCH_2$—$CH_2$), 69.09 (≡CH), 77.87 (Ar—CH—$CH_3$), 81.43 (≡C—$CH_2$), 108.87 (C-2), 110.81 (C-5), 118.49 (C-6), 136.12 (C-1), 148.34 (C-3), 149.12 (C-4).

4.) 1-{1-[(Z)-3-chloro-but-2-envyloxy]ethyl}-3,4-dimethoxybenzene

Into a flask equipped with stirrer 4.27 g (0.02345 mol) α-methylveratryl alcohol and 5.0 g (0.0469 mol)

2-chlorobut-2-en-1-ol (consisting mainly of the Z geometric isomer) are placed, and to the mixture 5.0 ml of the 50 w/v % calcium chloride-1 w/w % hydrochloric acid solution is added, at a fast rate. The mixture is stirred overnight at room temperature. Then it is diluted with ether, and the mixture is neutralized with a few drops of 1 M sodium hydroxide solution. The two phases are separated, the aqueous phase is thoroughly extracted with ether. The combined organic layers are washed with saturated sodium chloride, dried and evaporated. 5.7 g colourless oil is obtained. Yield:90%. Purity (GC) approx. 88.5%. GC (CP 9000, CP-SIL-5CB, 60 m×0.53 mm, 5 ml/min $N_2$, FID, 250° C.): IR (CHCl$_3$, cm$^{-1}$) υ: 2973, 2931, 2862, 2839, 1659, 1606, 1595, 1511, 1465, 1443, 1261, 1164, 1141, 1093, 1028. $^1$H-NMR (200 MHz, CDCl$_3$) δ: 1.43 (3H, d, J=6.5 Hz, CH—CH$_3$), 1.97 (3H, J=0.5 Hz, =CCl—CH$_3$), 3.80 (2H, m, OCH$_2$), 3.87 and 3.89 (altogether 6H , each s, OCH$_3$), 4.38 (2H, q, J=6.5 Hz, Ar—CHO), 5.78 (1 H, m, CH=CCl), 6.83 (2H, d, Ar), 6.87 (1H, d, Ar). $^{13}$C-NMR (50 MHz, CDCl$_3$) δ: 21.23 (=CCl—CH$_3$), 24.08 (CH—CH$_3$), 55.84 (OCH$_3$), 64.10 (OCH$_2$), 77.05 (Ar—CHO), 108.92 (C-2), 110.91 (C-5), 118.74 (C-6), 124.43 (CH=CCl), 134.0 (CH=CCl), 135.89 (C-1), 148.49 and 149.23 (C-3 and C-4).

5.) 1-[1-(But-2-ynyloxyethyl]3-methoxy-4-hydroxybenzene 4.0 g (23.6 mmol) of 1-(3-methoxy-4-hydroxyphenyl) ethyl alcohol is dissolved in 4.0 g of 2-butynol and to the solution 8.0 ml of the 50 w/v % of calcium chloride-1 w/w % hydrochloric acid solution is added under stirring at room temperature. The mixture is stirred overnight at that temperature. The reaction is followed by TLC method (eluent: n-hexane—ethyl acetate 7:3, R$_f$=0.55). To the mixture ether is added, until the oily organic phase dissolves and the reaction mixture is neutralized with 1 M sodium hydroxide solution. The two phases are separated, the aqueous phase is twice extracted with ether, the united organic phase is washed subsequently with water and saturated sodium chloride solution, dried over MgSO$_4$, filtered and evaporated.

Yield 4.8 g (92.0%) thick oil. GC (CP 9000, CP-SIL-5CB 60 m×0.53 mm, 5ml/min $N_2$ FID, 250° C.): t$_R$=4.3 min, >93%. IR (CDCl$_3$, cm$^{-1}$) υ: 3668, 3540, 2973, 2923, 2858, 2424, 2376, 2233, 1729, 1610, 1512, 1465, 1453, 1433, 1372, 1344, 1320, 1268, 1235, 1186, 1162, 1128, 1111, 1082, 1036, 1005, 970, 913, 886, 859, 822, 698, 645, 598. $^1$H-NMR (200 MHz, CDCl$_3$) δ: 1.45 (3H, d, J=6.5 Hz, CH—CH$_3$), 1.84 (3H, t, J=2.2 Hz ≡C—CH$_3$), 3.82 and 4.01 (2H, ABX$_3$, J$_{AB}$=15.0 Hz, J$_{AX}$=J$_{BX}$=2.3 Hz, ≡C—CH$_2$O), 3.88 (3H, s, OCH$_3$), 4.53 (2H, q, J=6.5 Hz, Ar—CHO), 6.76–6.89 (3H, m, aromatic). $^{13}$C-NMR (50 MHz, CDCl$_3$) δ: 3.57 (≡C—CH$_3$), 23.76 (CH—CH$_3$), 55.83 (OCH$_3$), 55.89 (≡C—CH$_2$O), 75.35 (≡C—CH$_2$), 76.40 (Ar—CH—CH$_3$) 81.91 (≡C—CH$_3$), 108.39 (C-2), 114.03 (C-5), 119.73 (C-6). 134.60 (C-1), 145.15 (C-4), 146.75 (C-3).

6.) 3,4-Dimethoxy-1-[1-(pent-3-ynyloxyl)ethyl]benzene

Into a flask, equipped with stirrer, 1.5 g (8.23 mmol) of α-methylveratryl alcohol and 1.4 g (16.46 mmol) of 3-pentyn-1-ol are placed and to the mixture 3.0 ml of the 50 w/v % calcium chloride-1 w/w % hydrochloric acid solution is added, at a fast rate. The mixture is stirred overnight at room temperature, then it is diluted with ether, and the mixture is neutralized with a few drops of 1 M sodium hydroxide solution. The two phases are separated, the aqueous phase is thoroughly extracted with ether. The united organic phase is washed with saturated sodium chloride solution, dried and evaporated.

Yield: 1.9 g (93%). GC (CP 9000, CP-SIL-5CB, 60 m×0.53 mm, 5 ml/min $N_2$, FID, 250° C.) t$_R$=5.0 min, approx. 93.2%. IR (CDCl$_3$, cm$^{-1}$) υ: 2995, 2974, 2957, 2864, 2838, 1607, 1595, 1510, 1465, 1260, 1163, 1142, 1098, 1027. $^1$H-NMR (200 MHz, CDCl$_3$) δ: 1.44 (3H, d, J=6.4 Hz, CH—CH$_3$), 1.75 (3H, t, J=2.5 Hz, CH$_3$—C≡), 2.37 (2H, m, CH$_2$—C≡), 3.38 (2H, t, J=7.2 Hz), 3.87 and 3.89 (altogether 6H , each s, OCH$_3$), 4.38 (2H, q, J=6.4 Hz, Ar—CHO), 6.83 (2H, d, aromatic), 6.90 (1H, s, aromatic). $^{13}$C-NMR(50 MHz, CDCl$_3$) δ: 3.42 (CH$_3$—C≡), 20.27 (OCH$_2$—CH$_2$), 24.07 (CH—CH$_3$), 55.78 és 55.85 (OCH$_3$), 67.04 (OCH$_2$—CH$_2$), 75.93 and 77.78 (Ar—CH—CH$_3$, C≡C two signals overlapping), 108.92 (C-2), 110.83 (C-5), 118.52 (C-6), 136.34 (C-1), 148.33 (C-3), 149.13 (C-4).

7.) 1-[1-(3-Butyn-2-yloxy)ethyl]-3,4-dimethoxybenze

Into a flask, equipped with stirrer, 3.0 g (0.0164 mol) of α-methylveratryl alcohol and 3.46 g (0.0493 mol) of 3-butyn-2-ol are placed and to the mixture 1.5 ml of the 50 w/v % of calcium chloride-1 w/w % hydrochloric acid solution is added, at a fast rate. The mixture is stirred overnight at room temperature, then it is diluted with 10 ml of ether, and neutralized with a few drops of 1 M sodium hydroxide solution. The two phases are separated, the aqueous phase is thoroughly extracted with ether. The united organic phase is washed with saturated sodium chloride solution, dried and evaporated. The residue is purified by coloumn chromatography (eluent:hexane-ethyl acetate 4:1, R$_f$=0.41 and 0.36).

The two diastereomers (threo-erythro) were partly separated:

More apolar (major) α-isomer 1.9 g,

60–40 mixture 0.76 g,

More polar, β-isomer 0.32 g.

Ratio of the two isomers, calculated on the basis of the isolated amounts: approx. 3.7:1

Yield: 2.98 g (0.0127 mol, 77.6%). GC (CP 9000, CP-SIL-5CB, 60 m×0.53 mm, 5 ml/min $N_2$, FID, 250° C.): α-isomer: t$_R$=3.4 min, approx. 97.27%, β-isomer: t$_R$=3.58 min, approx. 94.26%.

α-isomer:

IR (CHCl$_3$, cm$^{-1}$) υ: 3306, 2981, 2934, 2838, 1608, 1595, 1509, 1465, 1464, 1260, 1168, 1141, 1098, 1048, 963, 910, 860, 635. $^1$H-NMR (200 MHz, CDCl$_3$) δ: 1.39 (3H, d, J=6.6 Hz, ≡CCH—CH$_3$), 1.46 (3H, d, J=6.5 Hz, Ar—CH—CH$_3$), 2.41 (1H, d, J=2 Hz, ≡CH), 3.87 and 3.89 (altogether 6H , each s , OCH$_3$), 3.89 (1H, qd, J=2, 6.6 Hz, ≡CCH), 4.75 (2H, q, J=6.5 Hz, Ar—CH—CH$_3$), 6.80–6.89 (3H, m, aromatic). $^{13}$C-NMR (50 MHz. CDCl$_3$) δ: 22.19 (≡CCH—CH$_3$), 24.15 (Ar—CH—CH$_3$), 55.82 (OCH$_3$), 61.78 (≡C—CHO), 72.44 and 75.17 (≡CH and Ar—CHO), 84.11 (≡C—CH), 109.06 (C-2), 110.89 (C-5), 118.94 (C-6), 135.50 (C-1), 148.49 (C-3), 149.14 (C-4).

β-isomer:

IR(CHCl$_3$, cm$^{-1}$) υ: 3307, 2975, 2935, 2838, 1607, 1595, 1511, 1466, 1454, 1261, 1165, 1142, 1094, 1041, 961, 910, 862, 638. $^1$H-NMR (200 MHz, CDCl$_3$) δ: 1.44 (6H, d, J=6.5 Hz, ≡CCH—CH$_3$ and Ar—CH—CH$_3$), 2.355 (1H, d, J=2 Hz, ≡CH), 3.87 and 3.89 (altogether 6H, each s, OCH$_3$), 4.23 (1H, qd, J=2, 6.5 Hz, ≡CCH), 4.66 (2H, q, J=6.5 Hz, Ar—CH—CH$_3$), 6.79–6.96 (3H, m, aromatic). $^{13}$C-NMR (50 MHz, CDCl$_3$) δ: 21.83 (≡CCH—CH$_3$), 22.64 (Ar—CH—CH$_3$), 55.79 and 55.86 (OCH$_3$), 62.53 (≡C—CHO), 72.26 and 75.10 (≡CH and Ar—CHO), 84.40 (≡C—CH), 109.43 (C-2), 110.79 (C-5), 118.51 (C-6), 136.19 (C-1), 148.33 (C-3), 148.96 (C-4).

8.) 1-[1-(Prop-2-enyloxy)ethyl]-3,4-dimethoxybenzene, (1-(3',4'-dimethoxyphenyl)ethyl allyl ether)

Into a flask equipped with stirrer 3.0 3 (0.0164 mol) of α-methylveratryl alcohol and 1.9 g allyl alcohol are placed and to the mixture 1.5 ml of the 50 w/v % calcium chloride-1 w/v % hydrochloric acid solution is added, at a fast rate. The mixture is stirred overnight at room temperature, diluted with ether and neutralized with a few drops of 1 M sodium hydroxide solution. The two phases are separated, the aqueous phase is thoroughly extracted with ether. The united organic phase is washed with saturated sodium chloride solution, dried and evaporated.

Yield: 3.0 g (82.4%). GC (CP 9000, CP-SIL-5CB, 60 m×0.53 mnm, 5 ml/min $N_2$, FID, 250° C.) $t_R$=3.4 min approx. 90.3%. IR ($CHCl_3$, $cm^{-1}$) υ: 3079, 2996, 2973, 2933, 2860, 2838, 1607, 1595, 1510, 1465, 1443, 1419, 1311, 1260, 1164, 1141, 1089, 1027, 996, 928, 860. $^1$H-NMR (200 MNHz, $CDCl_3$) δ: 1.45 (3H, d, J=6.4 Hz, $CH_3$), 3.83 AB mid. (2H, ABdt, $J_{AB}$=12.7 Hz, J=1.3, 6.0 Hz, $OCH_2CH$=), 3.89 and 3.87 (altogether 6H, each s, $CH_3O$), 4.41 (2H, q, J=6.4 Hz, CH—O), 5.11–5.29 (2H, m), 5.81–6.0 (1H, m), 6.83 (2H, s), 6.89 (1H, s). $^{13}$C-NMR (50MHz, $CDCl_3$) δ: 24.0 (CH—$CH_3$), 55.77 ($OCH_3$), 69.17 ($OCH_2$=), 108.94 (C-2), 110.82 (C-5), 116.58 (CH=$CH_2$), 118.58 (C-6), 135.0 (C-1), 136.26 (CH=$CH_2$), 148.29 and 149.11 (C-3 and C-4).

9.) 1-[1-(But-2-ynyloxy)ethyl]naphthalene/1-(1-naphthyl)ethyl but-2-ynyl ether/

To a flask equipped with magnetic stirrer, condenser and drying tube filled with calcium chloride, α-methyl-1-naphthyl-methanol (0.86 g, 5 mmol) and 2-butyn-1-ol (0.7 g, 10 mmol are placed and dissolved in 15 ml of dichloroethane. Under stirring at room temperature zinc(II) chloride (0.68 g, 5 mmol) is added to the mixture. The reaction is accompanied by a characteristic change of colour. After 24 hours of reaction the organic phase is washed with 3×5 ml of saturated sodium chloride solution, dried and evaporated. The raw product (1.2 g) is purifed by coloumn chromatography.

Yield: 0.8 (3.57 mmol, 71%). GC 95%. IR ($CHCl_3$, $cm^{-1}$) υ: 3052, 2977, 2921, 2856, 1596, 1509, 1444, 1371, 1095, 1078. $^1$H-NMR (200 MHz, $CDCl_3$) δ: 1.67 (3H, d, J=6.5 Hz, $CH_3$—CH), 1.37 (31H, t, J=2.3 Hz, ≡C—$CH_3$), 2.96 and 4.15 (altogether 2H, ABX, $J_{AB}$=15.0 Hz, $J_{AX}$=$J_{BX}$32 2.3 Hz, $OCH_2$—C≡C), 5.40 (1H. q, J=6.5 Hz, $C_{10}H_7$—CH—O), 7.51 (3H, m), 7.61 (1H, d, J=6.8 Hz), 7.79 (1H, d, J=8.1 Hz), 7.89 (1H, dd, J=7.9, 1.8 Hz), 8.22 (1H, d, J=8.1 Hz) $^{13}$C-NMR (50 MHz, $CDCl_3$) δ: 3.64 (C≡C—$CH_3$), 22.96 ($CH_3$—CH), 56.37 (O—$CH_2$—C≡C), 74.29 ($CH_3$—CH), 75.36 and 82.14 (C≡C), 123.26 (C-8), 123.52, 125.50, 125.85, 127.92, 128.83, 130.78 (C-8a), 133.88 (C-4a), 138.42 (C-1).

10.) General procedure for the preparation of But-2-ynyl benzyl ethers

Into a flask equipped with stirrer 10 mmol of the benzyl alcohol given below and 1.2 g (20 mmol) of 2-butyn-1-ol are placed and to the mixture 1.5 ml of the 50 w/v % calcium chloride-1 w/w % hydrochloric acid solution is added, at a fast rate. The mixture is stirred overnight at room temperature. The reaction is followed by TLC method. The mixture is then diluted with ether and neutralized with a few drops of 1 M sodium hydroxide solution. The two phases are separated, the aqueous phase is thoroughly extracted with ether. The united organic phase is washed with saturated sodium chloride solution, dried and evaporated. The product obtained is purifed by coloumn chromatography.

a.)
Starting benzyl alcohol: 3,4-dimethoxybenzyl alcohol; Product: 3,4-dimethoxybenzyl but-2-ynyl ether; Yield: 85%; Purity (GC): 94%; IR ($CDCl_3$, $cm^{-1}$) υ: 3025, 3000, 2956, 2937, 2921, 2855, 2839, 1607, 1595, 1512, 1466, 1443, 1420, 1158, 1140, 1070, 1028. $^1$H-NMR (200 MHz, $CDCl_3$) δ: 1.84 (3H, t, J=2.3 Hz, C≡C—$CH_3$), 3.83 and 3.85 (altogether 6H, $CH_3O$), 4.08 (2H, q, J=2.3 Hz, $OCH_2$C≡C—), 4.48 (2H, s, aryl-$CH_2$), 6.77–6.88 (3H, m, aryl). $^{13}$C-NMR (50 MHz, $CDCl_3$) δ: 3.45 (C≡C—$CH_3$), 55.67 and 55.71 ($CH_3O$), 57.31 ($OCH_2$C≡C—), 71.22 (aryl-$CH_2$), 75.0 (C≡C—$CH_3$), 82.42 (C≡C—$CH_3$), 110.76 (C-2), 111.23 (C-5), 120.54 (C-6), 130.05 (C-1), 148.58 (C-4), 148.88 (C-3).

b.)
Starting benzyl alcohol: (3,4-dimethoxyphenyl)dimethylcarbinol; Product: 1-(3,4-dimethoxyphenyl)-1-methylethyl 2-(but-2-ynyl) ether; Yield: 85%; Purity (GC): 94%.

c.)
Starting benzyl alcohol: 1-[1-hydroxypropyl]-3,4-dimethoxybenzene; Product: 1-[1-(2-butynyloxy)-propyl]-3,4-dimthoxybenzene; Yield: 87%; Purity (GC): CP 9000, CP-SIL-5CB, 60 m×0.53 μm, 5 ml/min $N_2$, FID, 220° C. $t_R$=13.0 min, >95%. IR ($CHCl_3$, $cm^{-1}$) υ: 2999, 2959, 2935, 2875, 2856, 2839, 2240, 1608, 1595, 1513. 1465, 1261, 1234, 1162, 1142, 1061, 1028. $^1$H-NMR (200 MHz, $CDCl_3$) δ: 0.84 (3H, t, J=7.4 Hz, $CH_2CH_3$), 1.65 and 1.83 (altogether 2H, each m, $CH_2C_3$), 1.82 (3H, t, J=2.3 Hz, C≡C—$CH_3$), 3.84 and 3.86 (altogether 6H, s, $CH_3O$), 3.78 and 3.99 (altogether 2H, $ABX_3$, $J_{AB}$=15.0 Hz, $J_{AX}$=$J_{BX}$=2.3 Hz, $OCH_2$), 4.22 (1H, t, J=6.8 Hz, CH—O), 6.80–6.83 (3H, m, aromatic) (signals of ethyl acetate can be seen at 1.22 (t), 2.01 (s) and 4.08 (q) ppm). $^{13}$C-NMR (50 MHz, $CDCl_3$) δ: 3.55 (C≡C—$CH_3$), 10.23 ($CH_2CH_3$), 30.58 ($CH_2CH_3$), 55.77 ($OCH_3$), 56.03 ($OCH_2$), 75.41 (C≡C—$CH_3$), 81.71 (C≡C—$CH_3$), 82.24 (CH—O), 109.34, 110.64 (C-2, C-5), 119.63 (C-6), 133.95 (C-1), 148.44 and 149.09 (C-3, C-4).

d.)
Starting benzyl alcohol: 1-[1-hydroxy-2-methylpropyl]-3, 4-dimethoxybenzene Product: 1-[1-(2-butynyloxy)-2-methylpropyl]-3,4-dimethoxybenzene; Yield: 85%; Purity (GC): CP 9000, CP-SIL-5CB, 60 m×0.53 μm, 5 ml/min $N_2$, FID, 220° C., $t_R$=14.0.0 min, >91%. IR ($CDCl_3$, $cm^{-1}$) υ: 3029, 2995, 2958, 2937, 2871, 2857, 2839, 2238, 1606, 1595, 1510, 1466, 1443, 1420, 1263, 1238, 1157,1142, 1062, 1028. $^1$H-NMR (400 MHz, $CDCl_3$) δ: 0.65 and 0.97 (altogether 6H, each d, J=6.8 Hz, $CH(CH_3)_2$), 1.77 (3H, t, J=2.3 Hz, C≡C—$CH_3$), 1.87 (1H, m, $CH(CH_3)_2$), 3.80 and 3.81 (altogether 6H, each s, $OCH_3$), 3.71 and 3.95 (altogether 2H, $ABX_3$, $J_{AB}$=15.0 Hz, $J_{AX}$=$J_{BX}$=2.3 Hz, $OCH_2$), 3.90 (1H, d, J=8.1 Hz, CH—O), 6.68–6.78 (3H, m, aromatic). $^{13}$C-NMR (100 MHz, $CDCl_3$) δ: 3.39 (C≡C—$CH_3$), 18.87 and 19.16 (($CH(CH_3)_2$), 34.32 ($CH(CH_3)_2$), 55.61 ($OCH_3$), 56.11 ($OCH_2$), 75.44 (C≡C—$CH_3$), 81.37 (C≡C—$CH_3$), 86.25 (CH—O), 109.76 (C-5), 110.32 (C-2), 120.19 (C-6), 132.91 (C-1), 148.24 (C-4) és 148.80 (C-3).

e.)
Starting benzyl alcohol: 5-[1-hydroxyethyl]-1,3-benzodioxol; Product: 5-[1-(2-butynyloxy)ethyl]-1,3- benzodioxol; Yield: 84%; Purity (GC): 94%; IR (CHCl$_3$, cm$^{-1}$) υ: 2979, 2921, 2882, 1609, 1502, 1486, 1441, 1079, 1041, 941. $^1$H-NMR (400 MHz, CDCl$_3$) δ: 1.41 (3H, d, J=6.5 Hz, CHCH$_3$), 1.83 (3H, t, J=2.3 Hz, C≡C—CH$_3$), 3.80 and 3.99 (altogether 2H, ABX$_3$, J$_{AB}$=15 Hz, J$_{AX}$=J$_{BX}$= 2.3 Hz, OCH$_2$), 4.51 (1H, q, J=6.5 Hz, CHCH$_3$), 5.92 (2H, AB, OCH$_2$O), 6.74 (2H, AB, H-6, H-7), 6.83 (1H, s, H-4). $^{13}$C-NMR (100 MHz, CDCl$_3$) δ: 3.50 (C≡C—CH$_3$), 23.67 (CHCH$_3$), 55.80 (OCH$_2$), 75.18 (C≡C—CH$_3$), 76.16 (CH—O), 81.93 (C≡C—CH$_3$), 100.84 (OCH$_2$O), 106.47, 107.88 (C-4, 7), 119.90 (C-6), 136.63 (C-5), 146.94 and 147.77 (C-3a, 7a).

f.)

Starting benzyl alcohol: 1-[1-hydroxyethyl]-3,4-diethoxybenzene; Yield: 1-[1-(2-butynyloxy)ethyl]-3,4-diethoxybenzene; Yield: 86%; Purity (GC): 93%;

g.)

Starting benzyl alcohol: 1-[1-hydroxyethyl]-3,4-dimethoxy-6-propylbenzene; Product: 1-[1-(2-Butynyloxy) ethyl]-3,4-dimethoxy-6-propyl-benzene; Yield: 73%; Purit (GC): CP 9000, CP-SIL-5CB, 60 m×0.53 mm, 5 ml/min N$_2$, FID, 250° C., t$_R$=6.7 min, kb 95.4%. IR(CDCl$_3$, cm$^{-1}$) υ: 2961, 2933, 2873, 2331, 1610, 1511, 1466, 1261, 1132, 1098, 1047. $^1$H-NMR (400 MHz, CDCl$_3$) δ: 0.96 (3H, t, J=7.3 Hz, CH$_3$), 1.41 (3H, d, J=6.4 Hz, CH$_3$CHO), 1.58 (2H, sextet, J=7.4 Hz, CH$_2$—CH$_3$), 1.81 (3H, t, J=2.5 Hz, CH$_3$—C≡), 2.54 (2H, m, CH$_2$—Ar), 3.78 and 3.98 (2H, ABX$_3$, J$_{AB}$=15.0 Hz, J$_{AX}$=J$_{BX}$=2.3 Hz, ≡C—CH$_2$O), 3.83 (6H, s, OCH$_3$), 4.86 (H, q, J=6.5 Hz, Ar—CHO), 6.60 and 6.91 (2H, s, aryl). $^{13}$C-NMR (100 MHz, CDCl$_3$) δ: 3.46 (≡C—CH$_3$), 14.05 (CH$_3$), 23.70 and 24.97 (CH$_2$—CH$_3$ and CH$_3$CHOH), 34.03 (aryl-CH$_2$), 55.62, 55.69 and 55.80 (OCH$_3$ and ≡C—CH$_2$O) 71.60 (Ar—CH—CH$_3$), 75.46 (≡C—CH$_2$), 81.84 (≡C—CH$_3$), 108.45, 112.32 (C-2, C-5), 132.29, 132.33 (C-6, C-1), 147.60, 147.79 (C-4, C-3).

11.) 5-[(2-butynyloxy)methyl]-1,3-benzodioxol

To a flask equipped with magnetic stirred condenser and drying tube filled with calcium chloride, 3.0 g, (13.95 mmol) of piperonyl bromide, 2.0 g (27.9 mmol) of 2-butyn-1-ol and 50 ml of dichloroethane are placed. After the addition of zinc(II) oxide (1.1 g, 13.5 mmol) the suspension is stirred at room temperature for 1 hour. The reaction is accompanied by a characteristic chance of colour. The mixture is then filtered, the filtrate is evaporated. The residual oil is dissolved in 50 ml of ether, washed within 2×10 ml of water, dried and evaporated. Yield 2.3 g (11.2 mmol, 80.7%), GC 82%. IR(CHCl$_3$, cm$^{-1}$) υ: 2997, 2946, 2921, 2888, 2376, 1609, 1503, 1491, 1445, 1251, 1099, 1070, 1042, 937, 865, 810; $^1$H-NMR (400 MHz, CDCl$_3$) δ: 1.87 (3H, t, J=2.3 Hz, Me), 4.10 (2H, q, J=2.3 Hz, O—CH$_2$—C≡), 4.47, (2H, s, O—CH$_2$—Ar), 5.94 (2H, s, O—CH$_2$—O), 6.76 (1H, d, J=8 Hz, H-7), 6.81 (1H, dd, J=8.15 Hz, H-6), 6.86 (1H, J=1.5 Hz, H-4); $^{13}$C-NMR (100 MHz, CDCl$_3$) δ: 3.52 (Me), 57.29 (O—CH$_2$—C≡), 71.15 (O—CH$_2$—Ar), 82.54 (CH$_3$—C≡), 100.9 C-2, 107.95, 108.71 (C-4, 7), 121.66 (C-6), 131.39, (C-5), 147.15, 147.66 (C3a, C-7a);

12.) 1-[(2-butynyloxy)methyl]naphthalene

To a flask equipped with magnetic stirrer, condenser and drying tube filled with calcium chloride, bromomethylnaphthalene (1.0 g, 4.52 mmol), 2-butyn-1-ol (0.63 g, 9 mmol) and 10 ml of dichloroethane are placed. After the addition of zinc(II) oxide (4.0 g, 4.52 mmol) the suspension is stirred for 1 hour at room temperature, then it is refluxed for 1 hour. The reaction is accompanied by a characteristic change of colour. The mixture is then filtered, the filtrate is evaporated. The residual oil is dissolved in 15 ml of ether, washed with 2×50 ml of water, dried and evaporated. The product is purified by colooumn chromatography. Purity (GC) 95%. IR (CHCl$_3$, cm$^{-1}$) υ: 3044, 3001, 2945, 2920, 2854, 1598, 1509, 1356, 1166, 1086, 1067; $^1$H-NMR (400 MHz, CDCl$_3$) δ: 1.93 (3H, t, J=2.3 Hz, C≡C—CH$_3$), 4.22 (2H, q, J=2.1 Hz, O—CH$_2$—C≡C), 5.06 (2H, s, C$_{10}$H$_7$—CH$_2$—O), 7.45 (1H, t, J=8 Hz), 7.53 (3H, m), 7.84 (1H, d, J=8.1 Hz), 7.88 (3H, m), 7.88 (1H, d, J=7.7 Hz), 8.19 (1H, d, J=8.2 Hz); $^{13}$C-NMR (100 MHz, CDCl$_3$) δ: 3.6 (C≡C—CH$_3$), 57.71 (O—CH$_2$—C≡C), 69.72 C$_{10}$H$_7$—CH$_2$—O), 75.10 (O—CH$_2$—C≡C), 82.76 (O—CH$_2$—C≡C), 124.03, 125.10, 125.72, 126.19, 126.85, 128.43, 128.72, 131.79 (C-8a), 133.06, 133.70.

13.) 5-[2-(2-butoxyethoxy)ethoxymethyl]-6-propyl-1,3-benzodioxol, PBO a.)

To a flask equipped with magnetic stirrer, condenser and drying tube filled with calcium chloride, 2.98 g (14,02 mmol) of 5-chloromethyldihydrosafrol, 2,72 g (16,82 mmol) diethylene glycol monobutyl ether and 20 ml of dichloroethane are placed. After the addition of zinc(II) oxide (1.22 g, 15.0 mmol) the suspension is stirred for 24 hours at room temperature. The reaction is followed by TLC method and after the disappearance of the starting benzyl chloride the mixture is filtered, the filtrate is evaporated. The residual oil is dissolved in 25 ml of ether, washed with 2×50 ml of water, dried and evaporated. The product is distilled in vacuo. Bp: 180° C./1 Hgmm. The material is identical with the marketed PBO. Yield 4,0 g (90%). Purity (GC) 98%.

b.)

To a flask equipped with magnetic stirrer, condenser and drying tube filled with calcium chloride, 2,12 g (10,0 mmol) of 5-chloromethyldihydrosafrol, 2,42 g (15,0 mmol) diethylene glycol monobutyl ether are placed. After the addition of 0.97 g (15.0 mmol) of zinc(II) oxide the suspension is stirred for 12 hours at room temperature. The reaction is followed by TLC method and after the disappearance of the starting benzyl chloride the mixture is diluted with diethyl ether, filtered, the filtrate is washed with 2×50 ml of water, dried and evaporated. The product is distilled in vacuo. Bp: 180° C./1 Hgmm. The material is identical with the marketed PBO. Yield 2,8 g (91%). Purity (GC) 98%.

What is claimed is:

1. A process for the preparation of mixed ethers of general formula I:

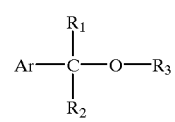

wherein
Ar represents an aromatic or one or more heteroatom-containing moiety, optionally substituted by one or more C$_{1-4}$ alkoxy, methylenedioxy, C$_{1-4}$ alkyl, halogen, C$_{1-4}$ haloalkyl or nitro-group, and/or condensed with a benzene ring; R$_1$ and R$^2$ independently mean hydrogen, C$_{1-4}$ alkyl, C$_{1-4}$ haloalkyl, C$_{2-4}$ alkenyl, phenyl, substituted phenyl, C$_{3-6}$ cycloalkyl group;
R$_3$ means C$_{3-6}$ alkynyl, optionally substituted by one or more C$_{1-6}$ alkyl, C$_{3-6}$ alkenyl, C$_{3-6}$ alkynyl, C$_{1-6}$ haloalkyl group, or halogen atom, R$_3$ also means a C$_{1-4}$ alkyloxy-C$_{1-4}$ alkyloxy-C$_{1-4}$ alkyl group;

comprising the step of:
reacting the compounds of general formula II with 1 to 3 molar equivalent of the alcohol of general formula III in the presence of acid, a Lewis acid, a metal oxide or a metal carbonate;

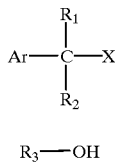

II $$R_3\text{—}OH$$

III isolating the resulting ether of general formula III; and
optionally, stabilizing the resulting ether of general formula III by the addition of a base and/or an antioxidant; and
wherein,
X means hydroxy, halogen or sulphonester leaving group.

2. The process according to claim 1, wherein said acid is a 0.01 to 3 molar equivalent of a strong mineral or organic acid.

3. The process according to claim 2, wherein said acid is hydrochloric acid, sulfuric acid, perchloric acid or an aromatic sulfonic acid.

4. The process according to claim 1, wherein the reaction step is performed in an aqueous solution of salts.

5. The process according to claim 4, wherein said aqueous solution of salts is a sodium chloride solution, a calcium chloride solution, a magnesium chloride solution or a zinc chloride solution.

6. The process according to claim 1, wherein the reaction step is performed in a 10 w/w % aqueous solution of the acid, saturated with an inorganic salt, at a temperature of −20° C. to 30° C.

7. The process according to claim 1, wherein the Lewis acid is a 0.01 to 3 molar equivalent of Zinc(II) chloride or an aromatic sulfonic acid and the reaction step is performed in an apolar aprotic solvent.

8. The process according to claim 7, wherein said aromatic sulfonic acid is benzenesulfonic acid or para-toluenesulfonic acid.

9. The process according to claim 7, wherein said apolar aprotic solvent is dichloroethane and the reaction step is performed at a temperature of −30° C. to 40° C.

10. The process according to claim 1, wherein said metal oxide is a 0.01 to 3 molar equivalent of zinc oxide and the reaction step is performed without solvent.

11. The process according to claim 1, wherein said metal oxide is a 0.01 to 3 molar equivalent of zinc oxide and the reaction step is performed in the presence of an apolar-aprotic solvent.

12. The process according to claim 11, wherein said apolar-aprotic solvent is dichloroethane.

13. The process according to claim 1, wherein said metal carbonate of zinc carbonate and the reaction step is performed without solvent.

14. The process according to claim 1, wherein said metal carbonate is zinc carbonate and the reaction step is performed in the presence of an apolar-aprotic solvent.

15. The process according to claim 14, wherein said apolar-aprotic solvent is dichloroethane.

16. The process according to claim 1, further comprising the step of: recovering the excess alcohol.

17. The process according to claim 6, wherein the inorganic salt is sodium chloride, calcium chloride or magnesium chloride.

* * * * *